United States Patent [19]

Kragen et al.

[11] 4,369,125
[45] Jan. 18, 1983

[54] GELLING COMPOSITIONS HAVING A BASE OF GALACTOMANNANS AND XANTHAN

[75] Inventors: Horst Kragen; Gérard Brigand, both of Carentan, France

[73] Assignee: C E C A-S.A., Velizy, France

[21] Appl. No.: 161,322

[22] Filed: Jun. 20, 1980

Related U.S. Application Data

[63] Continuation of Ser. No. 935,944, Aug. 25, 1978, abandoned.

[30] Foreign Application Priority Data

Sep. 12, 1977 [FR] France .............................. 77 27467

[51] Int. Cl.³ .............................................. B01J 13/00
[52] U.S. Cl. .................................... 252/316; 106/208;
149/19.7; 149/118; 426/573; 426/574
[58] Field of Search ........................ 252/316; 106/208

[56] References Cited

U.S. PATENT DOCUMENTS

| | | | |
|---|---|---|---|
| 3,000,790 | 9/1961 | Jeanes et al. | 435/104 |
| 3,096,293 | 7/1963 | Jeanes et al. | 252/316 |
| 3,265,631 | 8/1966 | Jordan | 252/316 |
| 3,519,434 | 7/1970 | Schuppner, Jr. | 426/574 |
| 3,557,016 | 1/1971 | Schuppner, Jr. | 252/316 |
| 3,623,868 | 11/1971 | Cronig | 430/353 |
| 3,726,690 | 4/1973 | Schuppner, Jr. | 426/583 |
| 3,765,918 | 10/1973 | Jordan et al. | 106/208 X |
| 3,784,712 | 1/1974 | Glicksman et al. | 426/167 |

FOREIGN PATENT DOCUMENTS

| | | | |
|---|---|---|---|
| 2119365 | 8/1972 | France | 426/167 |
| 2193074 | 2/1974 | France | 252/316 |

OTHER PUBLICATIONS

Van Wazer et al.: "Viscosity and Flow Measurement", Interscience Publishers, 1963, pp. 139-150 and 156-161.
"Les Techniques de l'Ingenieur", Nov. 1967, P3309-11 and P3309-12.
Rocks: "Xanthan Gum", Food Technology, vol. 25, May 1971, pp. 22, 23, 26, 28 and 31.

Primary Examiner—Richard D. Lovering
Attorney, Agent, or Firm—Fleit & Jacobson

[57] ABSTRACT

In a method for obtaining aqueous gels based on galactomannan and xanthan, the xanthan employed has first been subjected to a treatment resulting in partial or total deacetylation before being introduced in the mixture in which the ratio of deacetylated xanthan to galactomannan is within the range of 15/85 to 90/10. Potential applications include the food industry, explosives or air-treatment products.

8 Claims, 12 Drawing Figures

FIG_1

FIG_3

GELLING COMPOSITIONS HAVING A BASE OF GALACTOMANNANS AND XANTHAN

This is a continuation of application Ser. No. 935,944 filed Aug. 25, 1978, now abandoned.

This invention relates to the compositions which yield aqueous gels having a base of galactomannan and xanthan as well as to the gels obtained from these compositions and to the application of said gels.

Among the thickening agents currently in use, one well-known type consists of the galactomannans which are constituents of gums extracted from plants, e.g. guar gum, carob gum, tara gum, Espina corona gum.

Gelling agents which are also known include those obtained from glucides such as the sugars as a result of the action of a micro-organism; this is the case of xanthan, which is a polysaccharide obtained as a result of the action of bacteria of the Xanthomonas type.

It has been found possible to obtain gels of improved quality by associating xanthan and galactomannans; gels of this type have been described together with carob gum in U.S. Pat. Nos. 3,557,016, No. 3,726,690, U.S. Pat. No. 3,519,434, U.S. Pat. No. 3,623,868 as well as tara gum in French Pat. No. 2,119,365. These synergic effects have been reported in particular in the article by J. K. Rocks entitled "Xanthan gums" and published in the May, 1971 issue of "Food Technology", volume 25, pages 22-31, in which it is stated that it was not possible to obtain such effects with guar gum. However, the association of xanthan which has been subjected to a heat treatment and of a guar gum has been described in French Pat. No. 2,193,074.

It has been unexpectedly observed during tests that, by carrying out preliminary deacetylation of xanthan, much stronger gels than those obtained from xanthan could be obtained from the different gums of galactomannans, irrespective of the conditions of salinity and pH of the gels.

Xanthan is a polysaccharide which can be considered as an acetyl ester of a polymer containing mannose, glucose and glucuronic acid in the form of potassium salt. The acetyl groups represent approximately 4.7% of the polysaccharide; an alkaline treatment makes it possible to eliminate these acetylated groups and to obtain a xanthan which is either partly or wholly deacetylated. The method of deacetylation has been described in particular in U.S. Pat. No. 3,000,790 which states that deacetylated xanthan makes it possible to obtain viscous solutions which are less sensitive to inorganic salts than natural xanthan.

The object of the invention arises from the discovery that gels of higher strength than the association of natural xanthan and galactomannan can be obtained from the association of deacetylated xanthan with a galactomannan as a result of a synergic effect. It has been observed in particular that, whereas the association of natural xanthan and guar gum produces by means of a synergic effect solutions having high values of viscosity up to the point of formation of a very weak gel, strong gels can be obtained by means of deacetylated xanthan.

The interaction just mentioned represents an important advantage of the invention.

A more complete understanding of the invention will be gained from the following examples and from the accompanying FIGS. 1 to 12 which represent curves of cohesion and rigidity of the salts as a function of the mixture ratio and of the influence of certain agents.

In these examples, natural xanthan is designated as acetylated xanthan in order to emphasize the difference with respect to deacetylated xanthan whereas the term xanthan can designate either of these two products.

The viscosity ($\eta$) of xanthans, of galactomannans or of the association of these latter is measured at 20° C. with a Brookfield viscosimeter at 20 rpm on a 1 percent solution and is expressed in centipoises (cP).

The gels of the xanthan-galactomannan association are obtained by dispersion in the cold state at the dose of 1 percent followed by heating between 75° and 95° C. and cooling.

These gels have been characterized by:
their rigidity: this term designates the force which is necessary to cause a piston to penetrate into the gel over a distance of 8 mm, as measured by means of the instrument known as a Bloom gelometer and expressed in grams;
their cohesion: this term designates the compressive strength as measured by means of a Kobe apparatus by adding weights of 200 g at intervals of 15 seconds and expressed in kilograms.

EXAMPLE 1—INCREASE IN SYNERGY BETWEEN XANTHAN AND CAROB GUM

There were employed an acetylated xanthan and a deacetylated xanthan having a viscosity of approximately 1000 cP and a carob gum having a viscosity of approximately 1300 cP.

Figure 1:
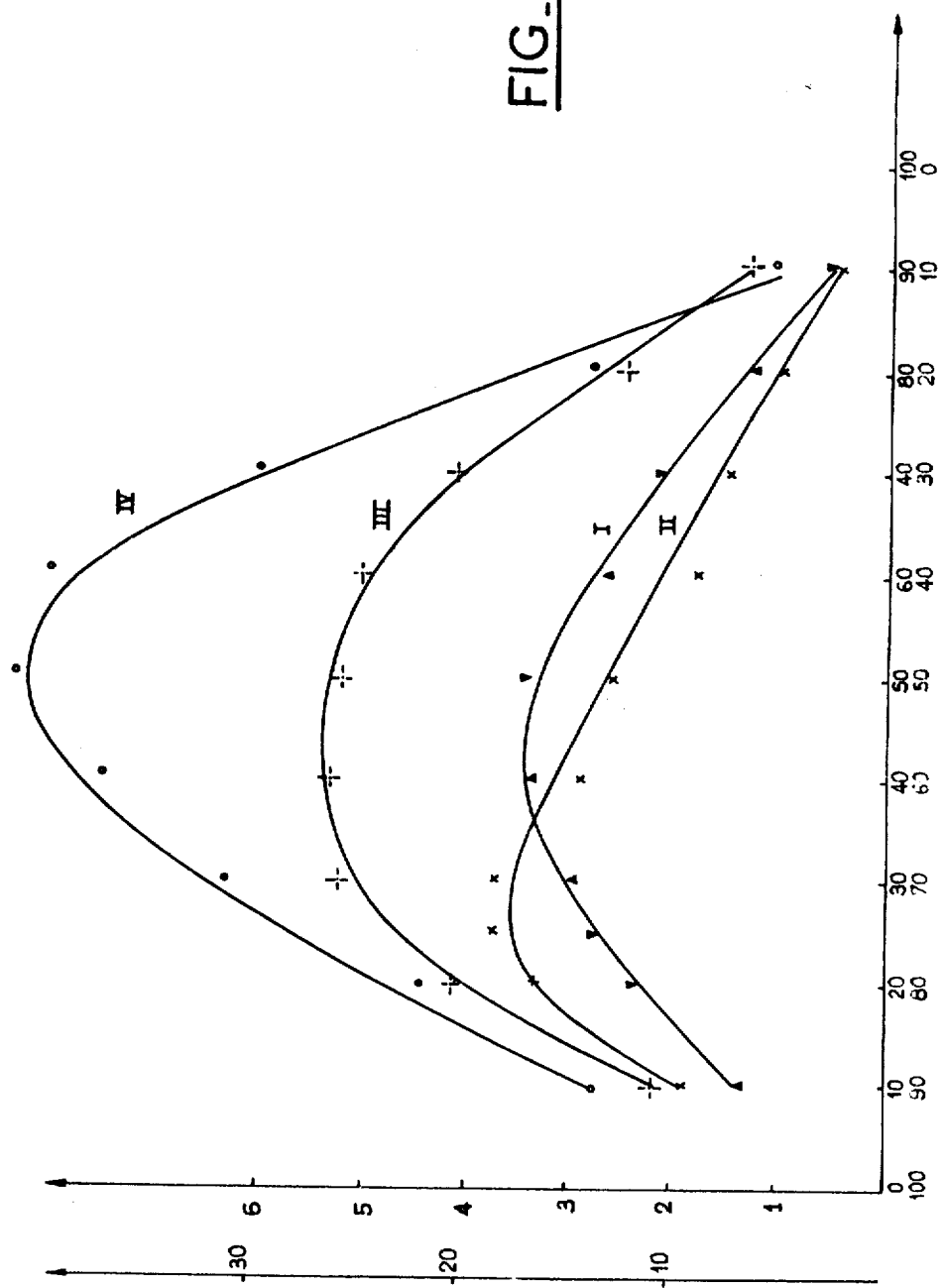
FIG. 1 shows curves of cohesion and rigidity, comparing xanthan and deacetylated xanthan in respect of different xanthan/carob gum ratios, using carob gum having a viscosity of 1300 cP.

A comparison between the acetylated xanthan and the deacetylated xanthan in respect of different xanthan/carob gum ratios is shown in Table I and in FIG. 1.

TABLE I

| Ratio of xanthan to carob gum | Rigidity (g) | | Cohesion (kg) | |
|---|---|---|---|---|
| | Acetylated xanthan | Deacetylated xanthan | Acetylated xanthan | Deacetylated xanthan |
| 10/90 | 14 | 22 | 1.9 | 2.8 |
| 20/80 | 23 | 41 | 3.3 | 4.4 |
| 30/70 | 30 | 52 | 3.7 | 6.3 |
| 40/60 | 34 | 53 | 2.9 | 7.5 |
| 50/50 | 34 | 52 | 2.6 | 8.3 |
| 50/40 | 27 | 50 | 1.8 | 8 |
| 70/30 | 21 | 41 | 1.5 | 6 |
| 80/20 | 13 | 25 | 1 | 2.8 |
| 90/10 | 5 | 13 | 0.5 | 1.1 |

EXAMPLE 2—INFLUENCE OF THE DEGREE OF POLYMERIZATION OF CAROB GUM

The increase in synergy is exhibited irrespective of the degree of polymerization of the carob gum.

Figure 2:
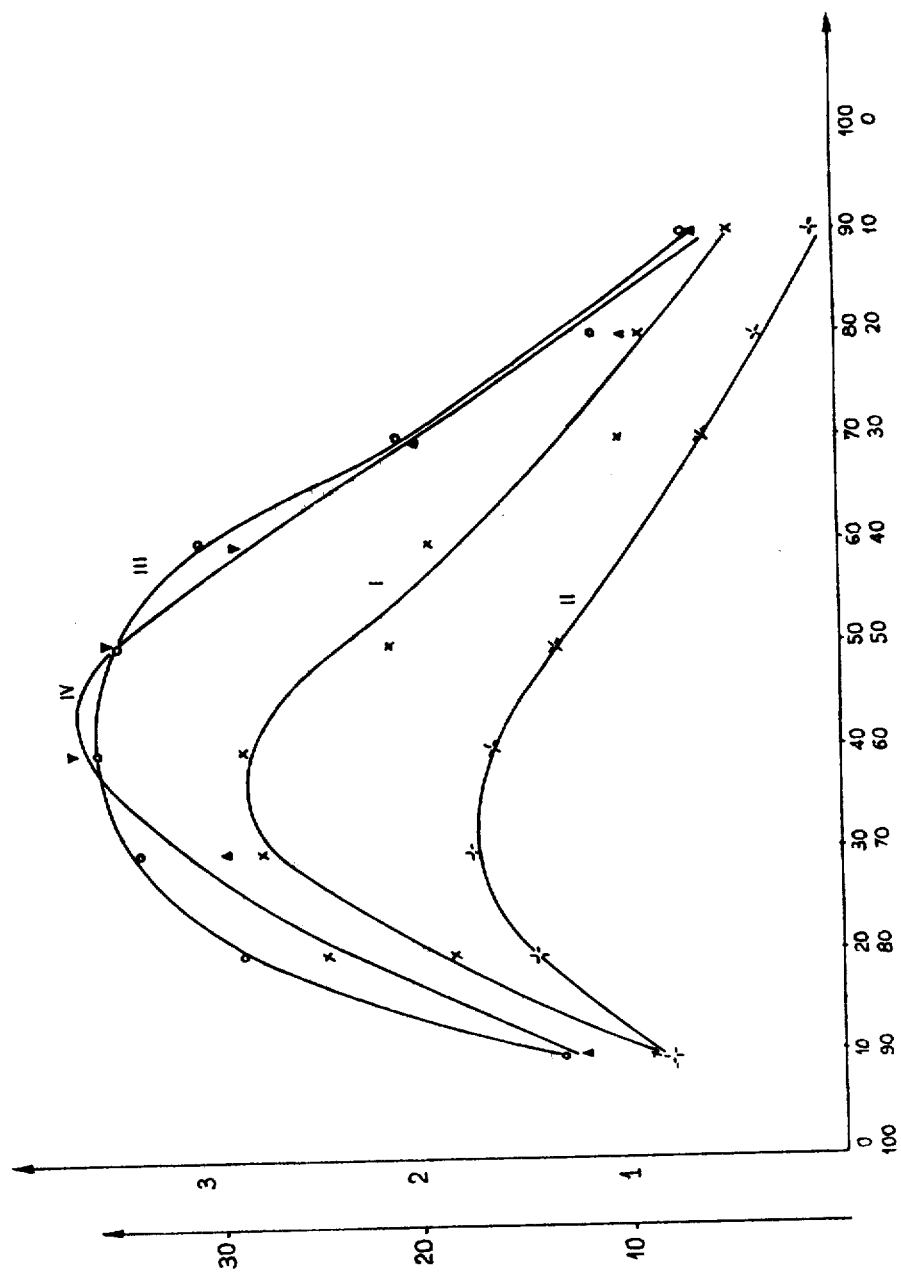
FIG. 2 shows curves of cohesion and rigidity, comparing xanthan and deacetylated xanthan in respect of different xanthan/carob gum ratios, using carob gum having a viscosity of 40 cP.

The test is carried out with a carob gum having a viscosity of 40 cP and produces the results of Table II and of FIG. 2.

TABLE II

| Ratio of xanthan to carob gum | Rigidity (g) | | Cohesion (kg) | |
|---|---|---|---|---|
| | Acetylated xanthan | Deacetylated xanthan | Acetylated xanthan | Deacetylated xanthan |
| 10/90 | 8 | 13 | 0.8 | 1.2 |
| 20/80 | 18 | 28 | 1.4 | 2.4 |
| 30/70 | 27 | 33 | 1.7 | 2.9 |
| 40/60 | 28 | 35 | 1.6 | 3.6 |
| 50/50 | 21 | 34 | 1.3 | 3.4 |
| 60/40 | 19 | 30 | 0.9 | 2.8 |
| 70/30 | 10 | 20 | 0.6 | 2.1 |
| 80/20 | 9 | 11 | 0.35 | 1 |
| 90/10 | 7 | 7 | 0.1 | 0.7 |

EXAMPLE 3—IMPROVEMENT OF THE SYNERGY BETWEEN XANTHAN AND GUAR GUM

Use was made of an acetylated xanthan and a deacetylated xanthan having a viscosity of 1300 cP and a guar gum having a viscosity of 3500 cP.

Figure 3:
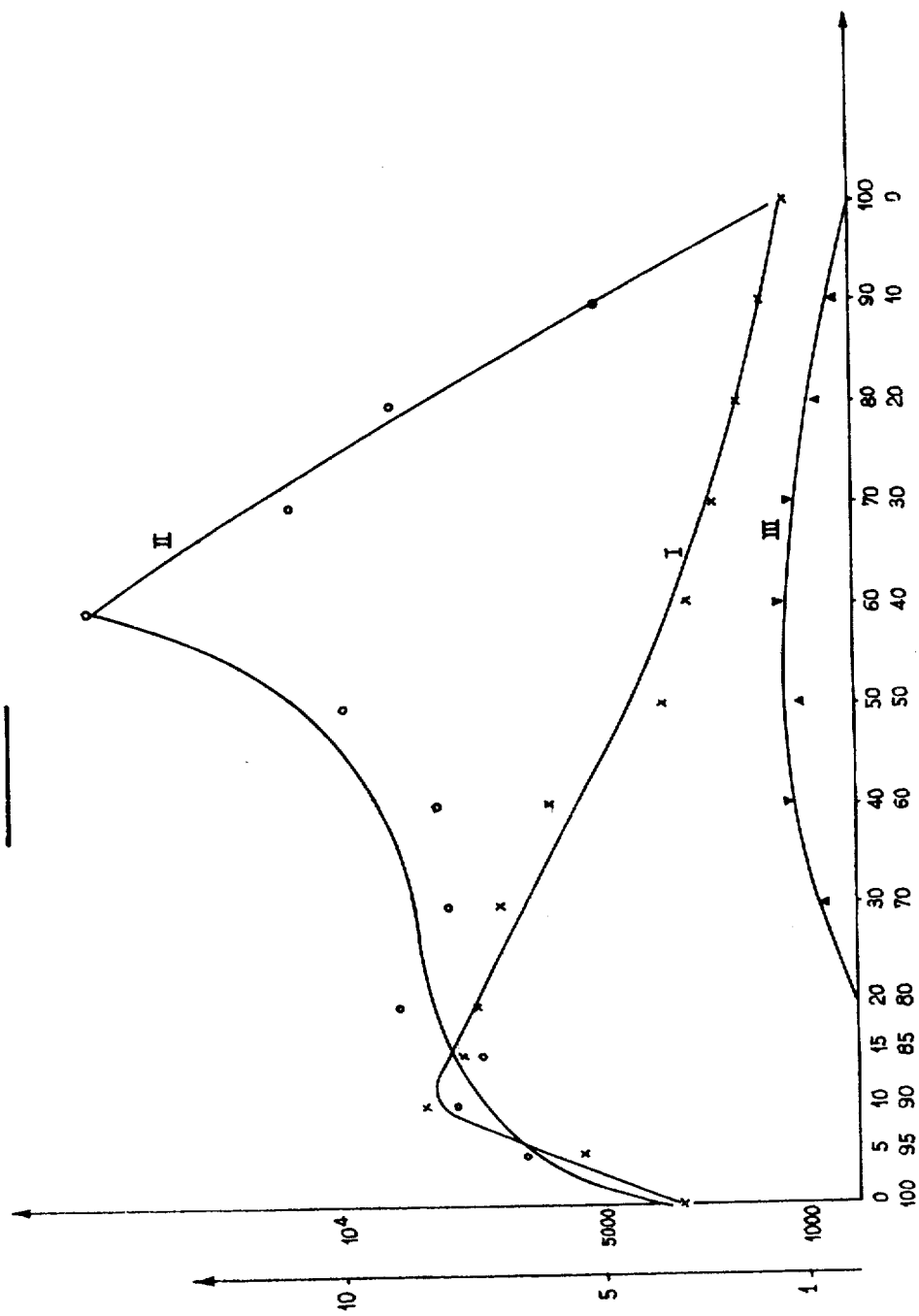
FIG. 3 shows curves of cohesion and rigidity, comparing xanthan and deacetylated xanthan in respect of different xanthan/guar gum ratios.

A comparison between the acetylated xanthan and the deacetylated xanthan in respect of different ratios of xanthan to guar gum is shown in Table III and in FIG. 3.

TABLE III

| Ratio of xanthan to guar gum | Viscosity of the solution or of the ground gel | | Cohesion of the gel (kg) | |
|---|---|---|---|---|
| | Acetylated xanthan | Deacetylated xanthan | Acetylated xanthan | Deacetylated xanthan |
| 5/95 | 5,400 | 6,500 | liquid | liquid |
| 10/90 | 8,500 | 7,900 | liquid | liquid |
| 15/85 | 7,800 | 7,400 | gel not measurable | liquid |
| 20/80 | 7,500 | 9,000 | liquid | liquid |
| 30/70 | 7,000 | 8,000 | liquid | 0.8 |
| 40/60 | 6,000 | 8,200 | liquid | 1.3 |
| 50/50 | 3,800 | 10,000 | liquid | 1.2 |
| 60/40 | 3,300 | 15,000 | liquid | 1.4 |
| 70/30 | 2,800 | 11,000 | liquid | 1.2 |
| 80/20 | 2,300 | 9,000 | liquid | 0.8 |
| 90/10 | 1,800 | 5,000 | liquid | 0.4 |

EXAMPLE 4—IMPROVEMENT OF THE SYNERGY BETWEEN XANTHAN AND TARA GUM

Use was made of an acetylated xanthan and a deacetylated xanthan having a viscosity of 1000 cP and a tara gum having a viscosity of 600 cP.

Figure 4:
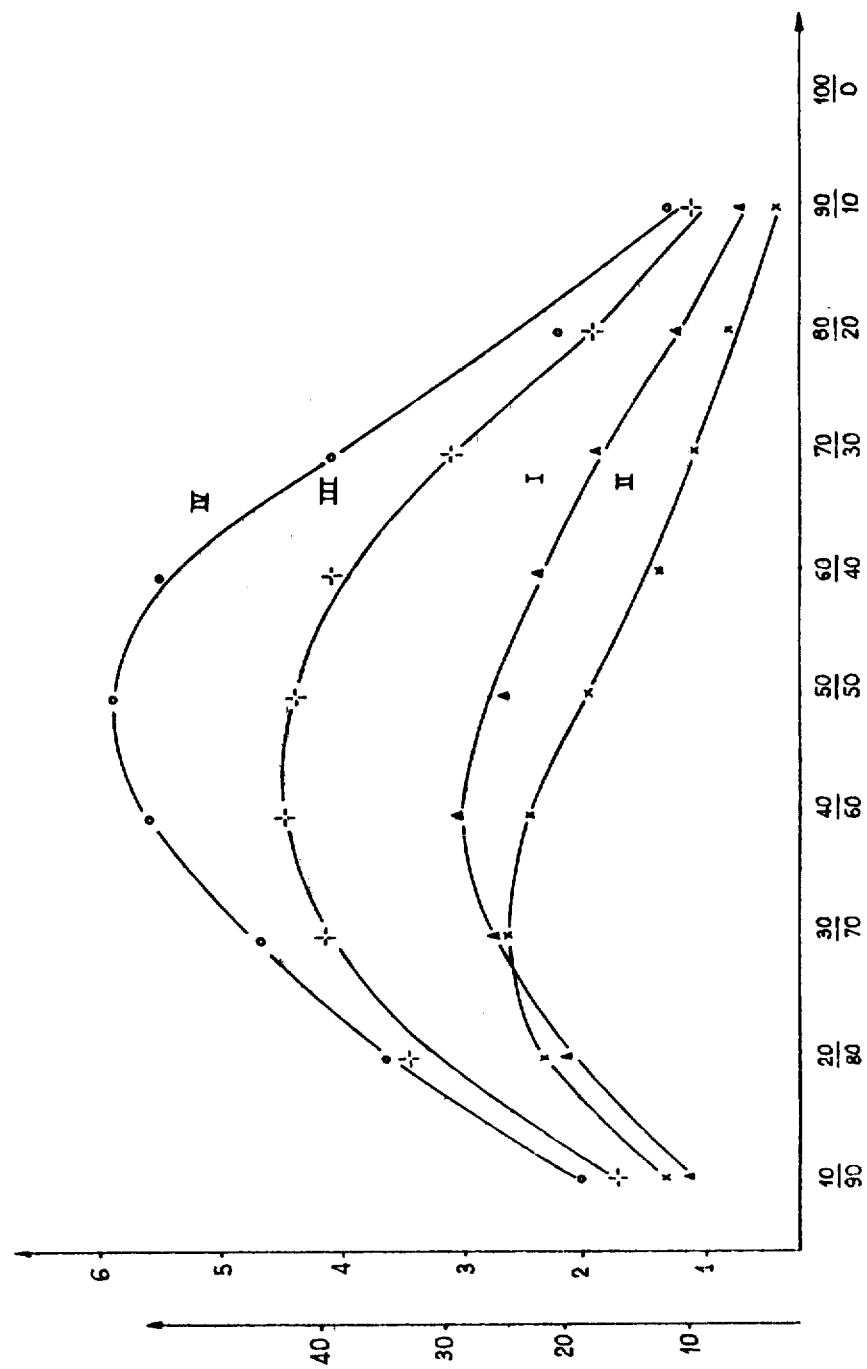
FIG. 4 shows curves of cohesion and rigidity, comparing xanthan and deacetylated xanthan in respect of different xanthan/tara gum ratios.

A comparison between the acetylated xanthan and the deacetylated xanthan in respect of different ratios of xanthan to tara gum is shown in Table IV and in FIG. 4.

TABLE IV

| Ratio of xanthan to tara gum | Rigidity (g) | | Cohesion (kg) | |
|---|---|---|---|---|
| | Acetylated xanthan | Deacetylated xanthan | Acetylated xanthan | Deacetylated xanthan |
| 10/90 | 11 | 17 | 1.3 | 2 |
| 20/80 | 21 | 34 | 2.3 | 3.6 |
| 30/70 | 27 | 41 | 2.6 | 4.6 |
| 40/60 | 30 | 44 | 2.4 | 5.5 |
| 50/50 | 26 | 43 | 1.9 | 5.8 |
| 60/40 | 23 | 40 | 1.3 | 5.4 |
| 70/30 | 18 | 30 | 1 | 4 |
| 80/20 | 11 | 18 | 0.7 | 2.1 |
| 90/10 | 6 | 10 | 0.3 | 1.2 |

EXAMPLE 5—IMPROVEMENT OF THE SYNERGY BETWEEN XANTHAN AND ESPINA CORONA GUM

Use was made of an acetylated xanthan and a deacetylated xanthan having a viscosity of 1000 cP and an Espina corona gum having a viscosity of 800 cP.

Figure 5:
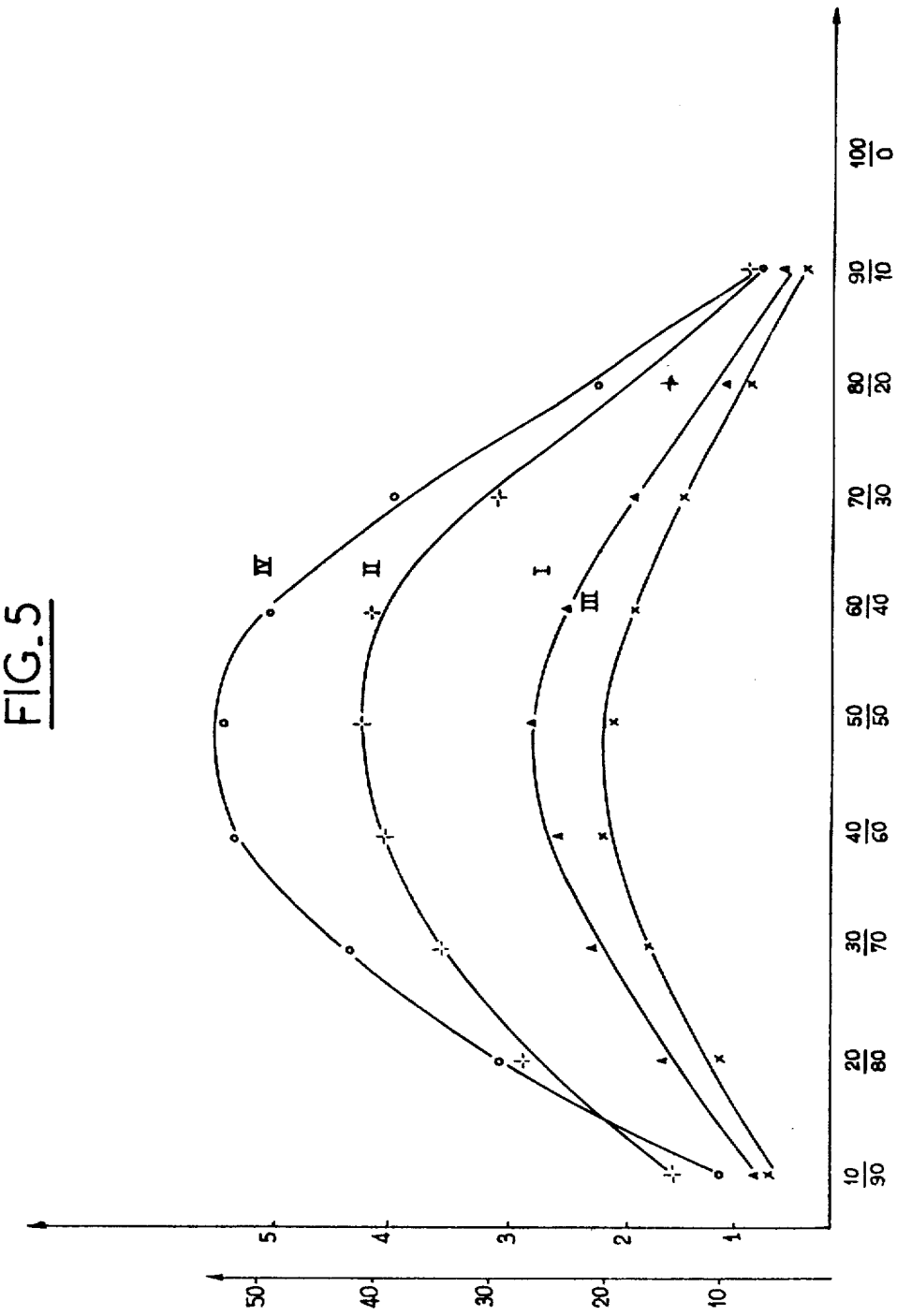
FIG. 5 shows curves of cohesion and rigidity, comparing xanthan and deacetylated xanthan in respect of different xanthan/Espina corona gum ratios.

A comparison between the acetylated xanthan and the deacetylated xanthan in respect of different ratios of xanthan to Espina corona gum is shown in Table V and in FIG. 5.

TABLE V

| Ratio of xanthan to Espina corona gum | Rigidity (g) | | Cohesion (kg) | |
|---|---|---|---|---|
| | Acetylated xanthan | Deacetylated xanthan | Acetylated xanthan | Deacetylated xanthan |
| 10/90 | 8 | 15 | 0.7 | 1.1 |
| 20/80 | 16 | 28 | 1.1 | 3 |
| 30/70 | 22 | 35 | 1.7 | 4.3 |
| 40/60 | 25 | 40 | 2.1 | 5.3 |
| 50/50 | 27 | 42 | 2 | 5.4 |
| 60/40 | 24 | 41 | 1.8 | 5 |
| 70/30 | 18 | 30 | 1.4 | 3.9 |
| 80/20 | 10 | 15 | 0.8 | 2.1 |
| 90/10 | 5 | 8 | 0.3 | 0.7 |

EXAMPLE 6

The use of gels in industry or in food usually calls for a medium containing salts and especially sodium chloride.

Figure 6:
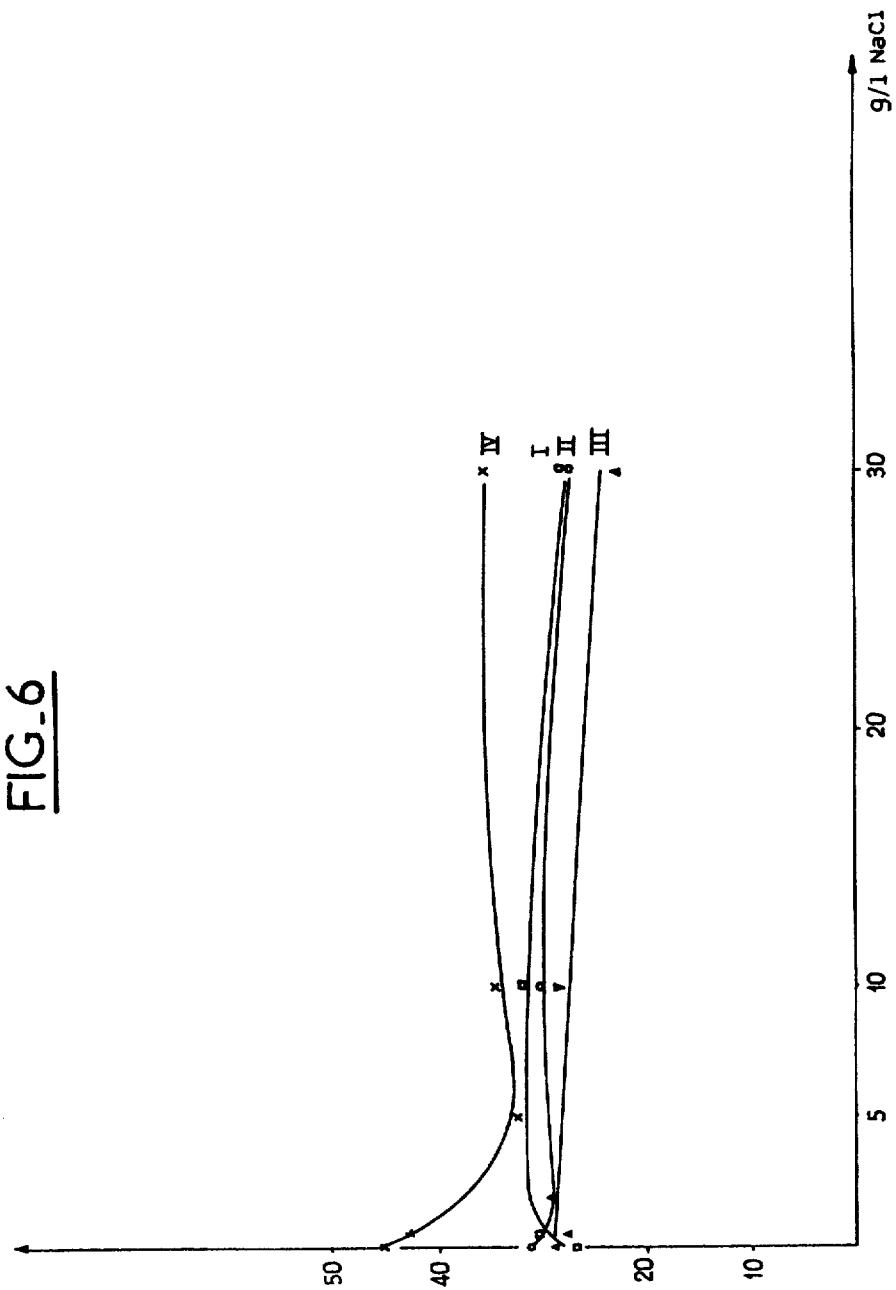
FIG. 6 gives result of rigidity measurements comparing xanthan and deacetylated xanthan in 50/50 mixtures with carob gum in respect of different doses of NaCl in the gel.
Figure 7:
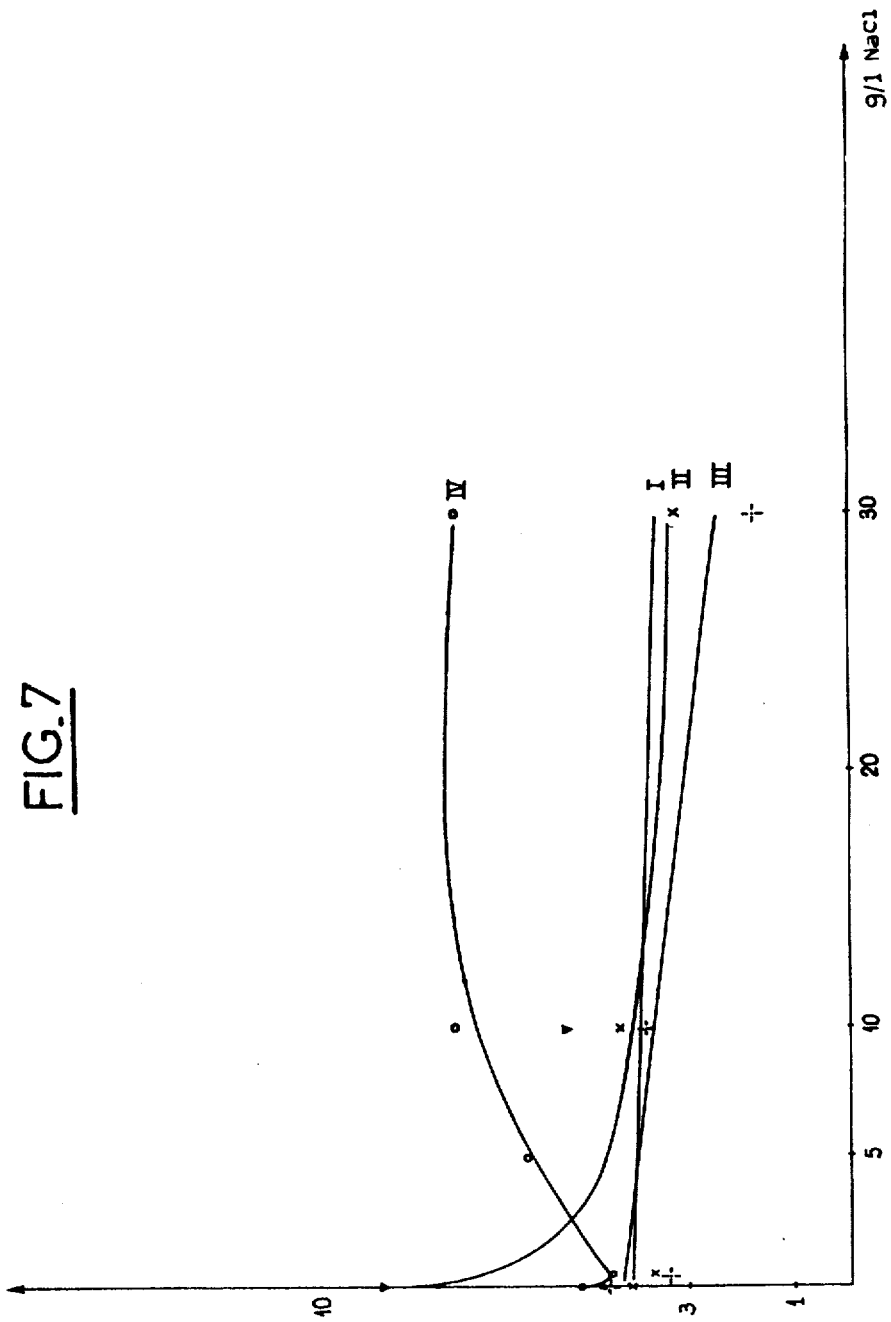
FIG. 7 gives result of cohesion measurements comparing xanthan and deacetylated xanthan in 50/50 mixtures with carob gum in respect of different doses of NaCl in the gel.

A study of the influence of electrolytes such as sodium chloride has been carried out with a 50/50 mixture of xanthan and carob gum. Three samples of acetylated xanthan have been compared with deacetylated xanthan in respect of different doses of sodium chloride in the gel. FIG. 6 gives the result of measurements of rigidity and FIG. 7 shows the result of measurements of cohesion.

These two figures show the superiority of gels having a base of deacetylated xanthan. However, by reason of the fact that the starting products do not necessarily have the same characteristics (Brookfield viscosity), a more rigorous example consists in starting from natural xanthan which is progressively deacetylated with 0.015 N sodium hydroxide (the deacetylation is followed over a period of time).

Figure 8:
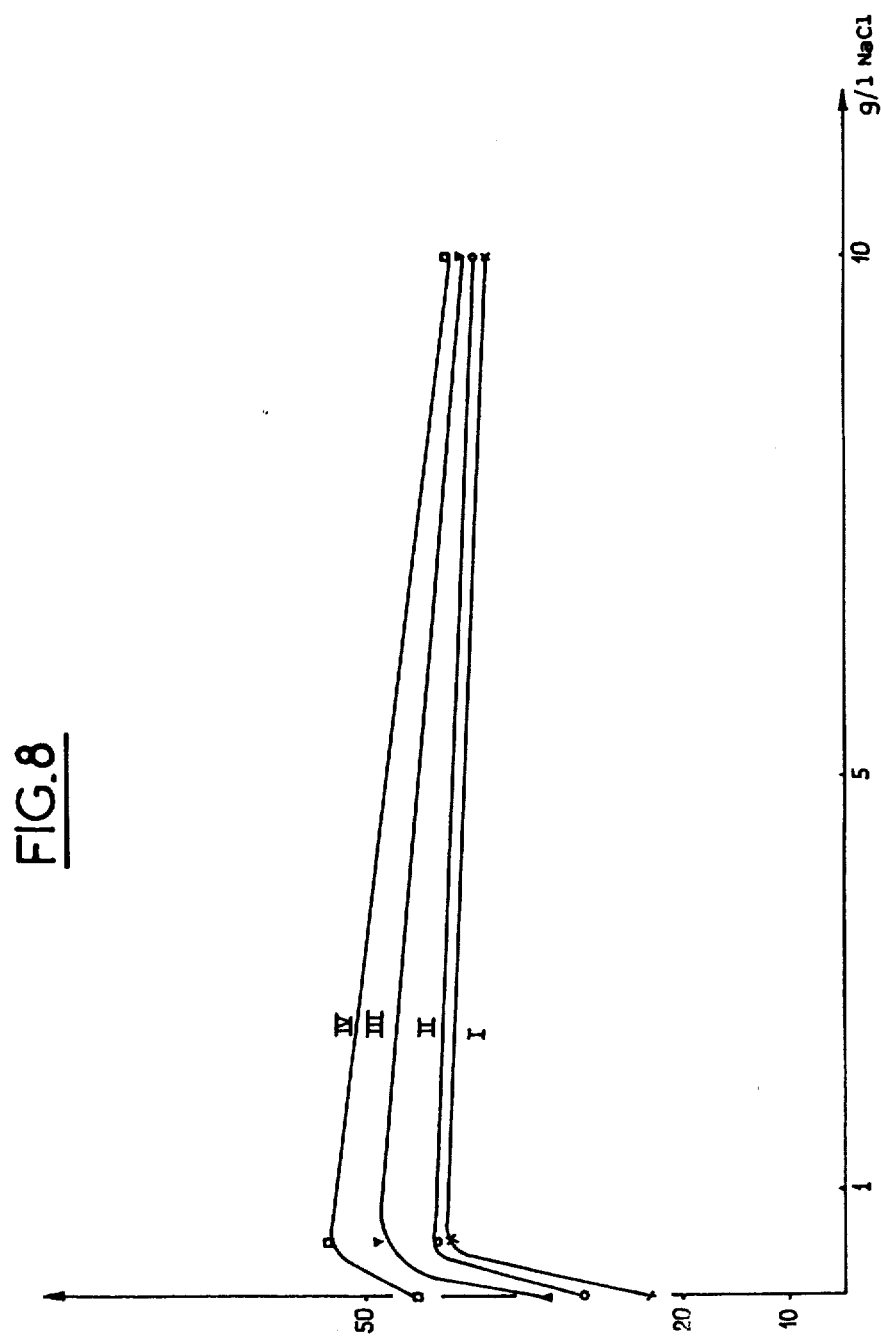
FIG. 8 gives result of rigidity measurements comparing acetylated xanthan with deacetylated xanthan.
Figure 9:
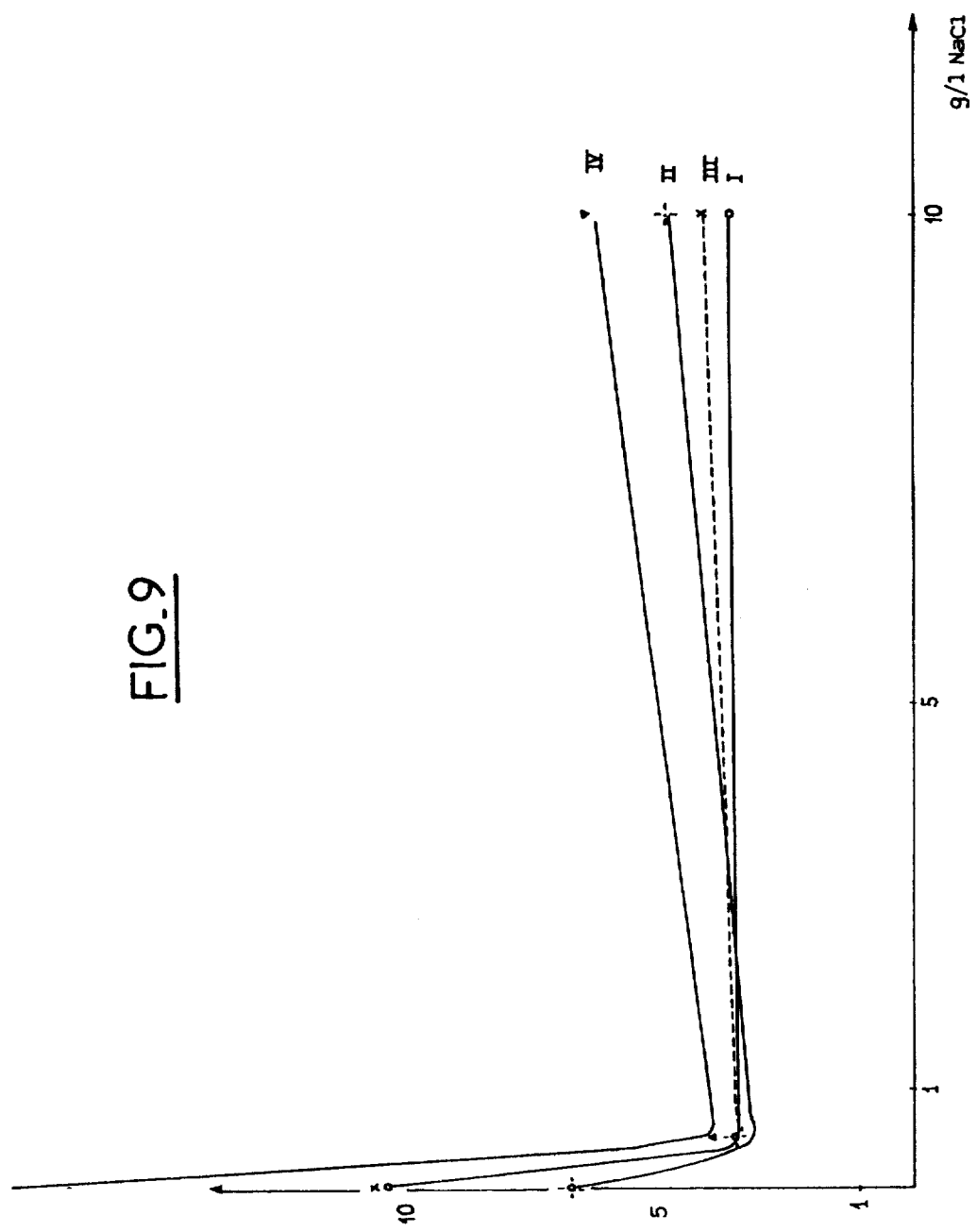
FIG. 9 gives result of cohesion measurements comparing acetylated xanthan with deacetylated xanthan.

A comparison has been made between the characteristics of an acetylated xanthan and of three samples of more or less deacetylated xanthan obtained from this acetylated xanthan. FIG. 8 gives the result of measurements of rigidity and FIG. 9 gives the result of measurements of cohesion.

The advantage of deacetylation is readily apparent from the different proportions of sodium chloride and as a function of the degree of deacetylation.

EXAMPLE 7

Figure 10:
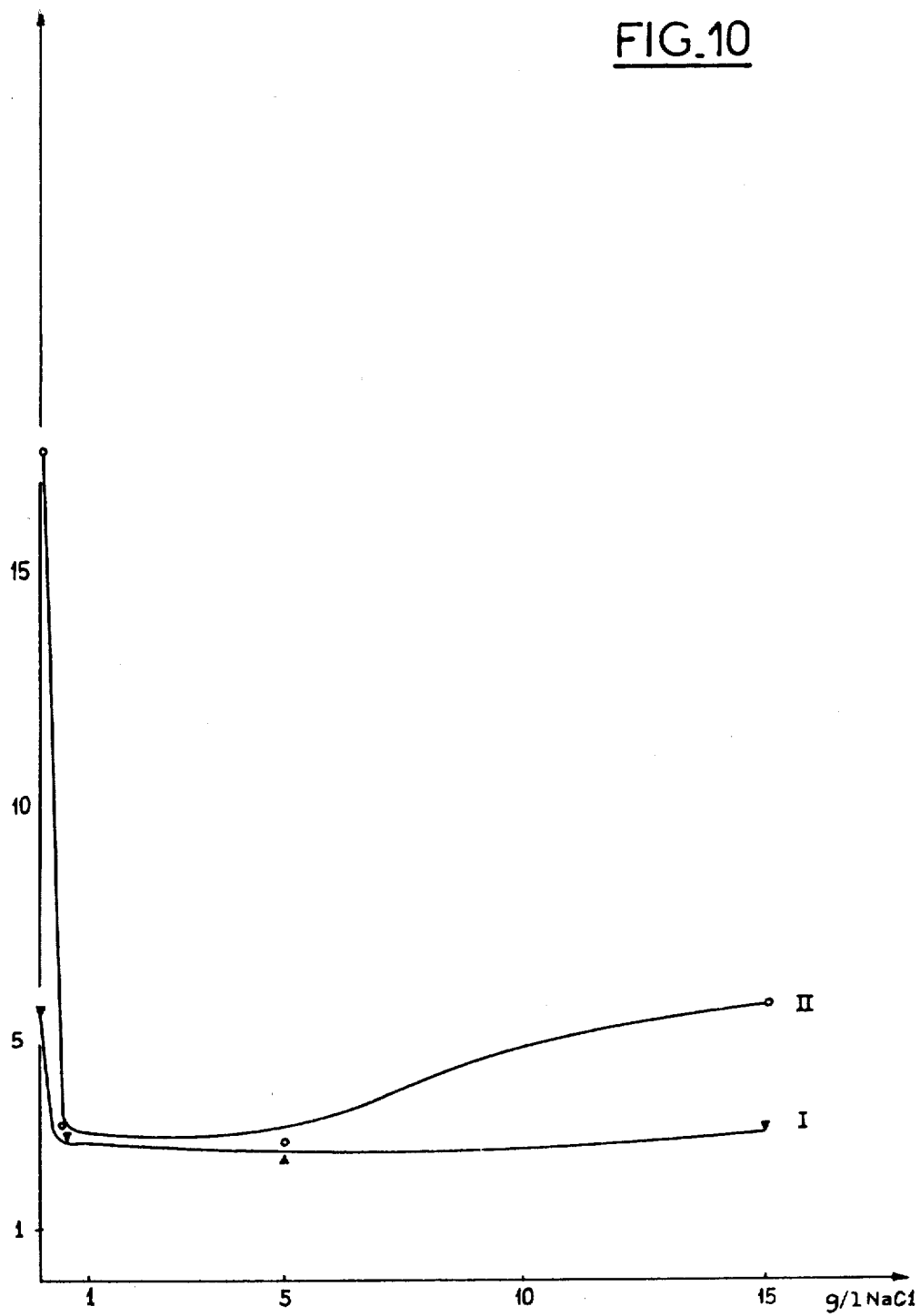
FIG. 10 gives results of cohesion measurements comparing acetylated xanthan with deacetylated xanthan in 50/50 association with carob gum in NaCl.
Figure 11:
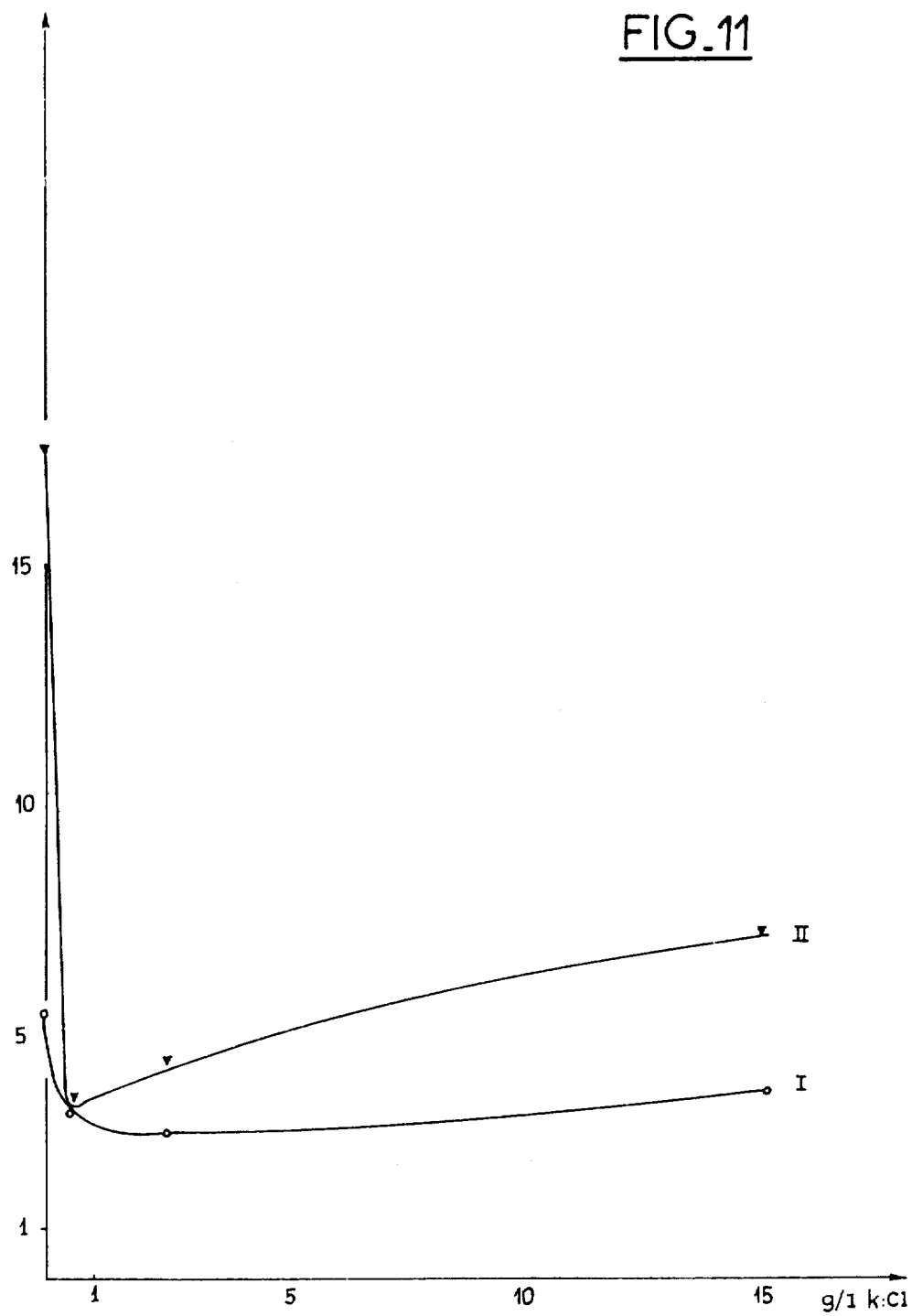
FIG. 11 gives results of cohesion measurements comparing acetylated xanthan with deacetylated xanthan in 50/50 association with carob gum in KCl.
Figure 12:
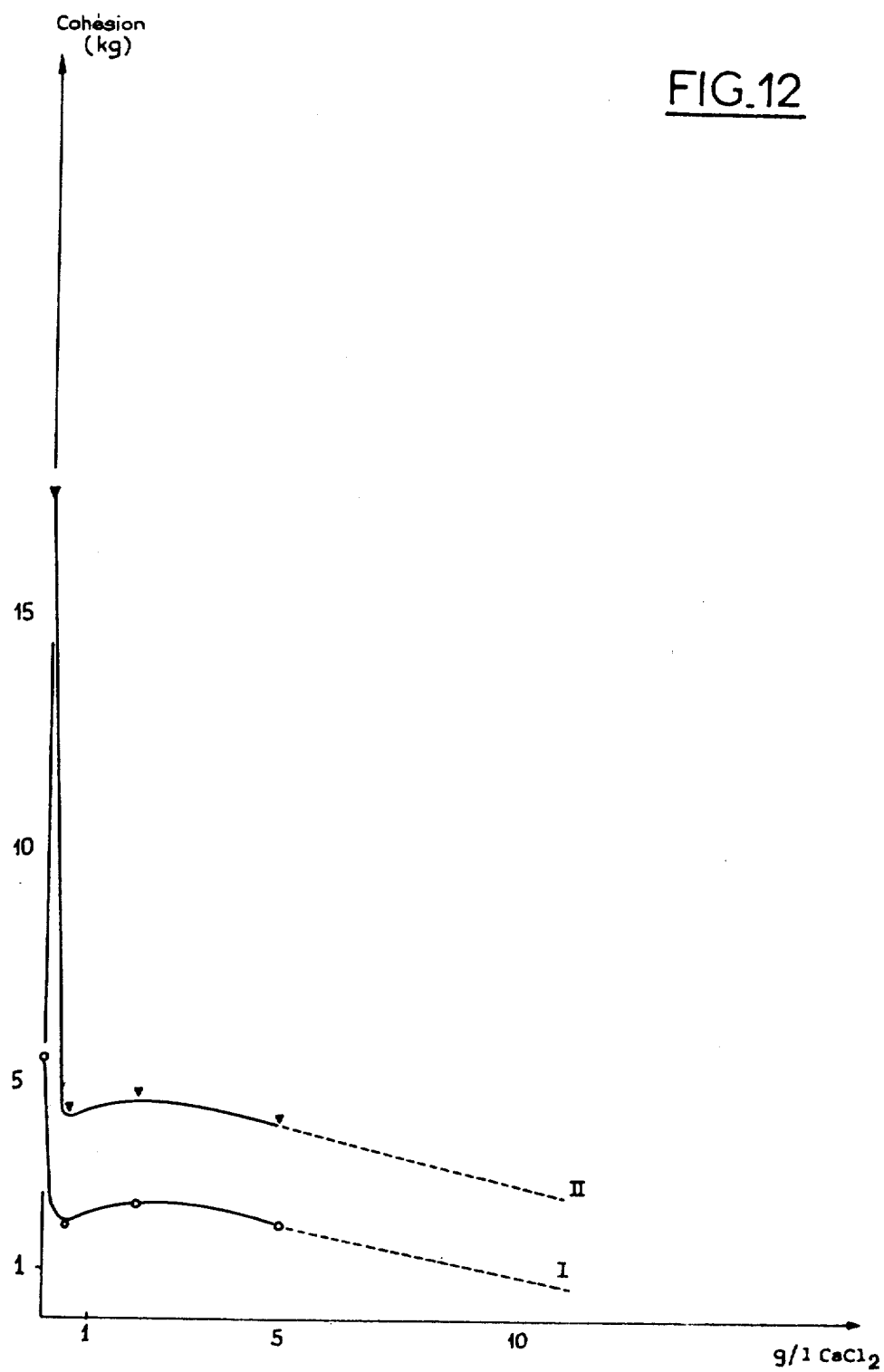
FIG. 12 gives results of cohesion measurements comparing acetylated xanthan with deacetylated xanthan in 50/50 association with carob gum in $CaCl_2$.

A study of the influence of the electrolytes was carried out by comparing a sample of acetylated xanthan and a sample of deacetylated xanthan employed in a 50/50 association with carob gum in respect of different proportions of sodium chloride, potassium chloride and calcium chloride. FIGS. 10, 11 and 12 give the results obtained in the case of each of these three salts and show that the cohesion is higher with deacetylated xanthan in respect of each of these three salts. The same applies to the rigidity as shown in Table VI.

TABLE VI

| Salt | g/l | Acetylated xanthan | Deacetylated xanthan |
|---|---|---|---|
| Standard reference | 0 | 20 | 41 |
| NaCl | 0.5 | 30 | 46 |
|  | 5 | 29 | 39 |
|  | 15 | 28 | 38 |
| KCl | 0.5 | 31 | 50 |
|  | 5 | 35 | 48 |
|  | 15 | 37 | 45 |
| CaCl$_2$ | 0.5 | 21 | 26 |
|  | 2 | 21 | 27 |
|  | 5 | 22 | 27 |

EXAMPLE 8—INFLUENCE OF THE USUAL ANIONS ON A GEL OF DEACETYLATED XANTHAN AND OF CAROB GUM

Ordinary anions do not produce any change in reactivity of deacetylated xanthan with respect to the carob gum.

Table VII gives the results obtained with a 50/50 mixture of deacetylated xanthan and carob gum to which are added various sodium salts in a quantity such that the proportion of Na$^+$ with respect to the gum is constant and corresponds to 5 g/l of NaCl.

TABLE VII

| Salt added | Rigidity (g) | Cohesion (kg) |
|---|---|---|
| Standard reference | 20 | 5.5 |
| Chloride | 30 | 3 |
| Carbonate | 25 | 2.9 |
| Nitrate | 32 | 3.2 |
| Acetate | 28 | 3.3 |
| Sulphate | 33 | 3.3 |
| Monosulphate | 29 | 2.6 |
| Sodium citrate | 30 | 2.6 |

This table shows that the reactivity of deacetylated xanthan with the galactomannans is not affected by the various anions employed.

The gels of deacetylated xanthan plus galactomannans can have a practically infinite variety of consistency according to the galactomannan employed, the proportion of xanthan to galactomannan and the total dose of gum employed. These gels can consequently find an application in the food industry, for example in pork-meat gels (aspics) or jelly-type desserts, or in the technical field, for example in explosive gels or gels for air-treatment products.

We claim:

1. A gelling composition consisting essentially of xanthan and a galactomannan gum selected from the group consisting of carob gum, tara gum, Espina Corona gum and mixtures thereof, wherein said xanthan has been subjected to a total or partial deacetylation treatment and wherein the ratio of deacetylated xanthan to galactomannan is from about 15/85 to 90/10.

2. The composition of claim 1, wherein the ratio of deacetylated xanthan to galactomannan is from about 40/60 to 60/40.

3. A gelling composition according to claim 1, wherein the carob gum employed has a degree of polymerization such that in a 1% solution the viscosity of said gum measured at 20° C. with a Brookfield viscosimeter at 20 rpm is within the range of 20 to 6000 centipoises.

4. By way of novel products, the gels obtained from the compositions according to claim 1 and employed in solution in an aqueous medium at a concentration within the range of 0.1 to 4%.

5. A method of obtaining aqueous gels having a base of a galactomannan gum and xanthan, said galactomannan gum selected from the group consisting of carob gum, tara gum, Espina Corona gum and mixtures thereof, the method comprising the steps of subjecting the xanthan to a total or partial deacetylation treatment, mixing the deacetylated xanthan with the galactomannan at a ratio of from about 15/85 to 90/10; combining the resulting mixture with an aqueous phase; heating the resulting mixture to from about 75° to 90° C.; and cooling.

6. The method of claim 5, wherein the ratio of deacetylated xanthan to galactomannan is from about 40/60 to 60/40.

7. A method according to claim 5, wherein the carob gum employed has a degree of polymerization such that in a 1% solution the viscosity of said gum measured at 20° C. with a Brookfield viscosimeter at 20 rpm is within the range of 20 to 6000 centipoises.

8. By way of novel products, the gels obtained according to claim 5 at a concentration of the association of deacetylated xanthan and galactomannan within the range of 0.1 to 4%.